US00PP07851P

United States Patent [19]

Simmons

[11] Patent Number: Plant 7,851

[45] Date of Patent: Apr. 7, 1992

[54] APPLE TREE DS-165

[75] Inventor: Daniel E. Simmons, Rogers, Ohio

[73] Assignee: Inter-Plant Patent Marketing, Inc., Niagara-On-The-Lake, Canada

[21] Appl. No.: 357,241

[22] Filed: May 25, 1989

[51] Int. Cl.[5] ..... A01H 5/00
[52] U.S. Cl. ..... Plt./34
[58] Field of Search ..... Plt. 34, 35

[56] References Cited

U.S. PATENT DOCUMENTS

P.P. 2,803 4/1968 Gibson ..... Plt. 35
P.P. 4,914 11/1982 Auffet ..... Plt. 34

*Primary Examiner*—Howard J. Locker

[57] ABSTRACT

An apple tree 'DS 165' bearing russet-resistant fruit is disclosed. The apple tree displays vigorous spurring and has short internode distances resulting in a more compact tree.

6 Drawing Sheets

This distinct new apple cultivar was discovered as a limb mutation of "Smoothee" in the orchard of Daniel E. Simmons, Peace Valley Orchards, R.R. #1, Rogers, Ohio. In comparison to "Smoothee," the mutation identified as DS-165 is a semi-spur type tree and the fruit has fewer, less conspicuous lenticels resulting in a smoother, more attractive fruit finish. This new selection has been asexually reproduced by limb grafting at Rogers, Ohio, on a variety of rootstocks and remains true to the description herein contained.

The accompanying photographs (FIG. 1: View of a lateral branch depicting fruiting habit of DS-165 on Malling 106 rootstock; trees in 3rd leaf; and FIG. 2: Another view depicting fruiting habit of DS-165 on Malling 106 rootstock; trees in 3rd leaf) show the increased development of fruiting spurs on 4 year old trees of DS-165 on MM 106 rootstocks.

Figure 1:
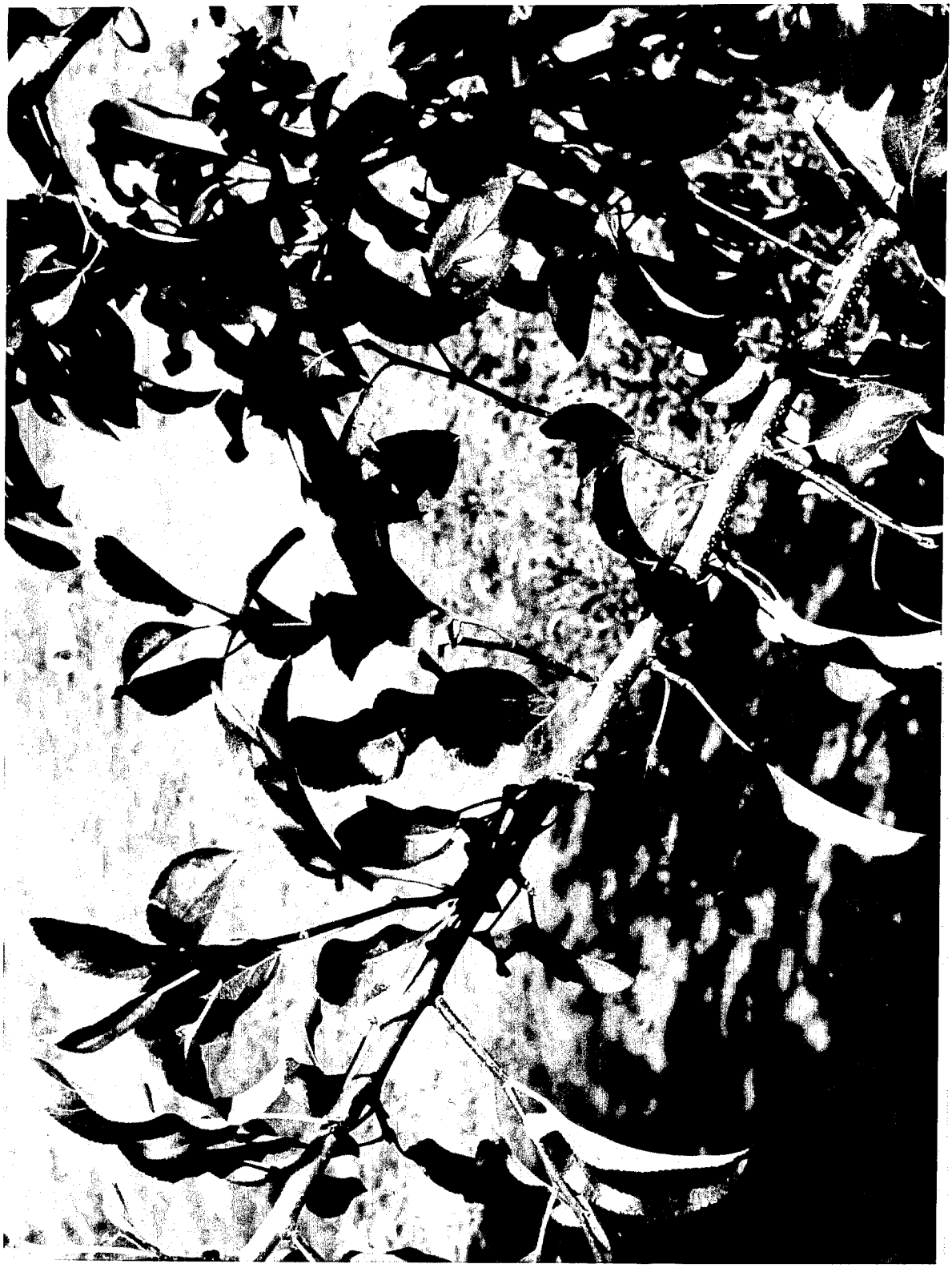
Figure 2:
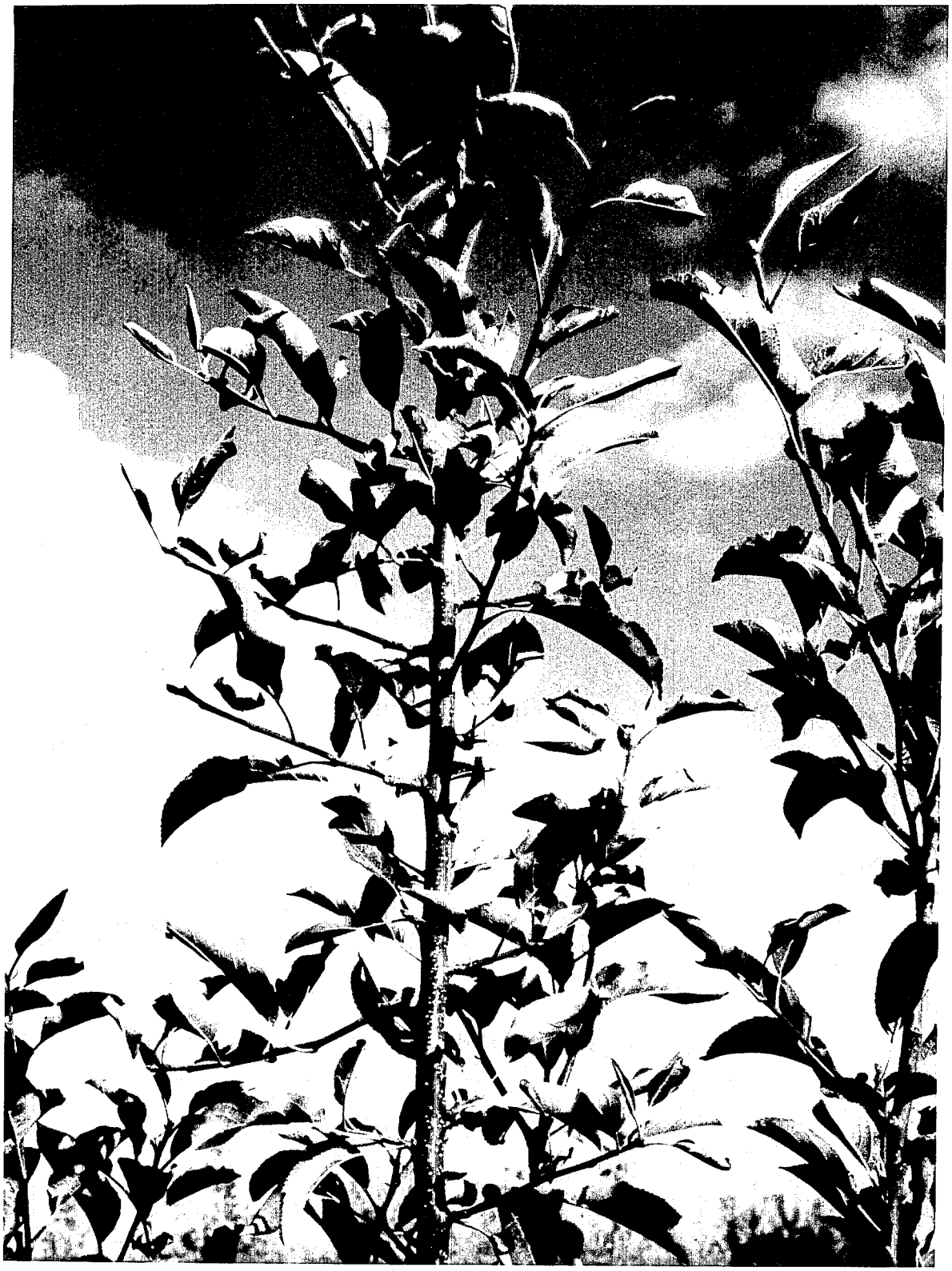
Figure 3:
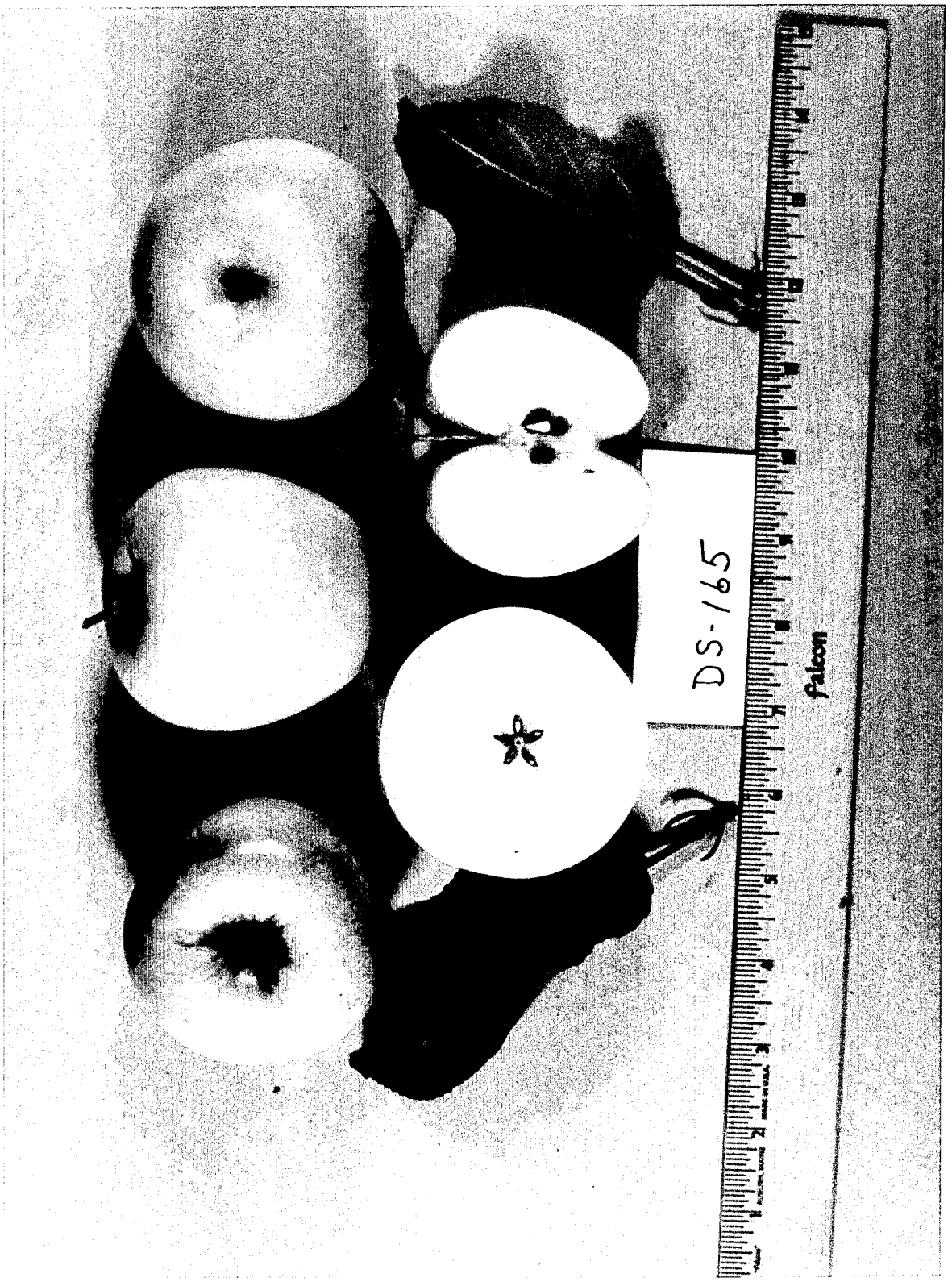
FIG. 3 shows typical examples of fruit and foliage of DS-165.
Figure 4:
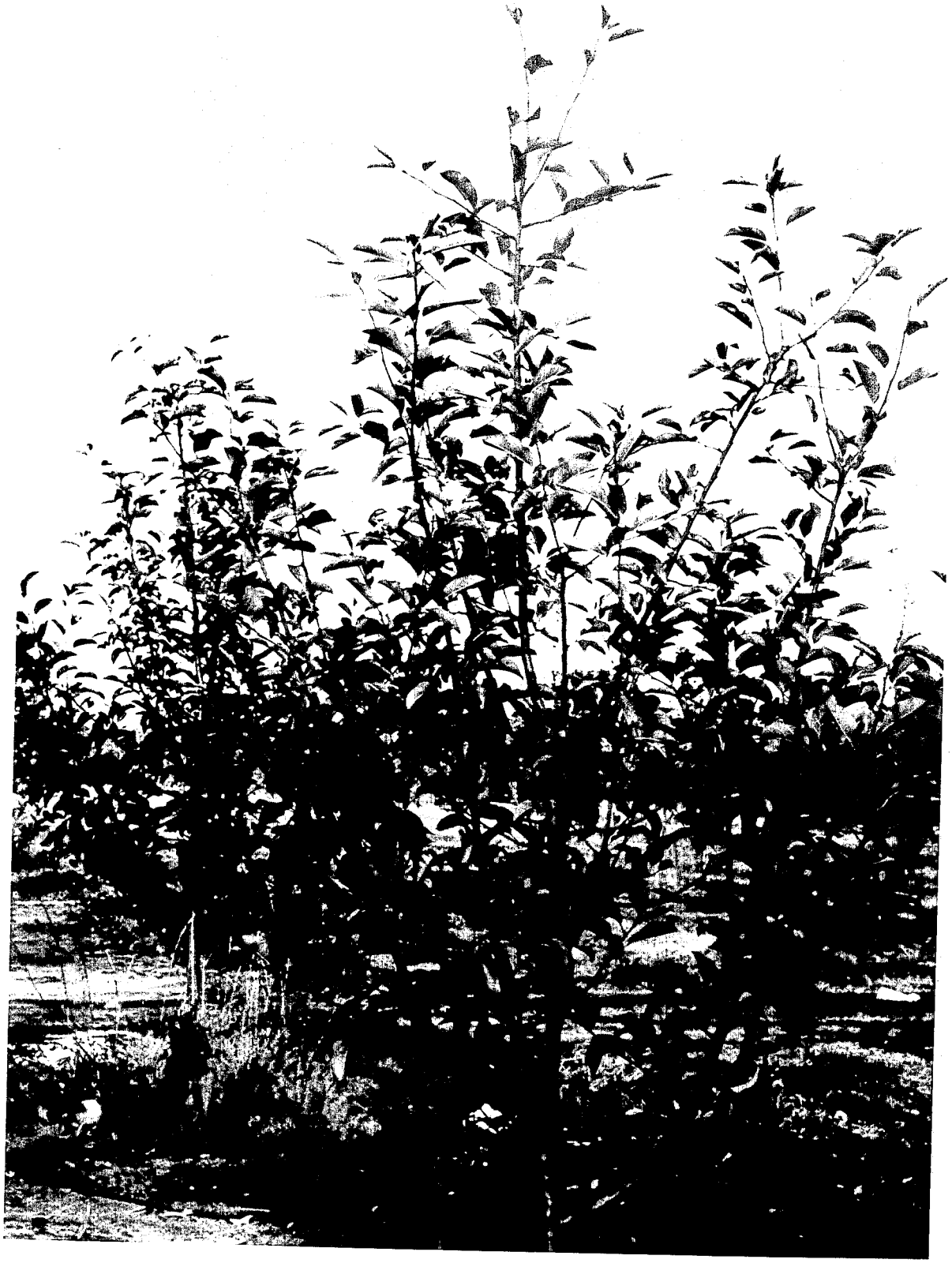
FIG. 4 is a whole tree view depicting growth habit of DS-165 Apple Tree on Malling 106 rootstock in 3rd leaf.
Figure 5:
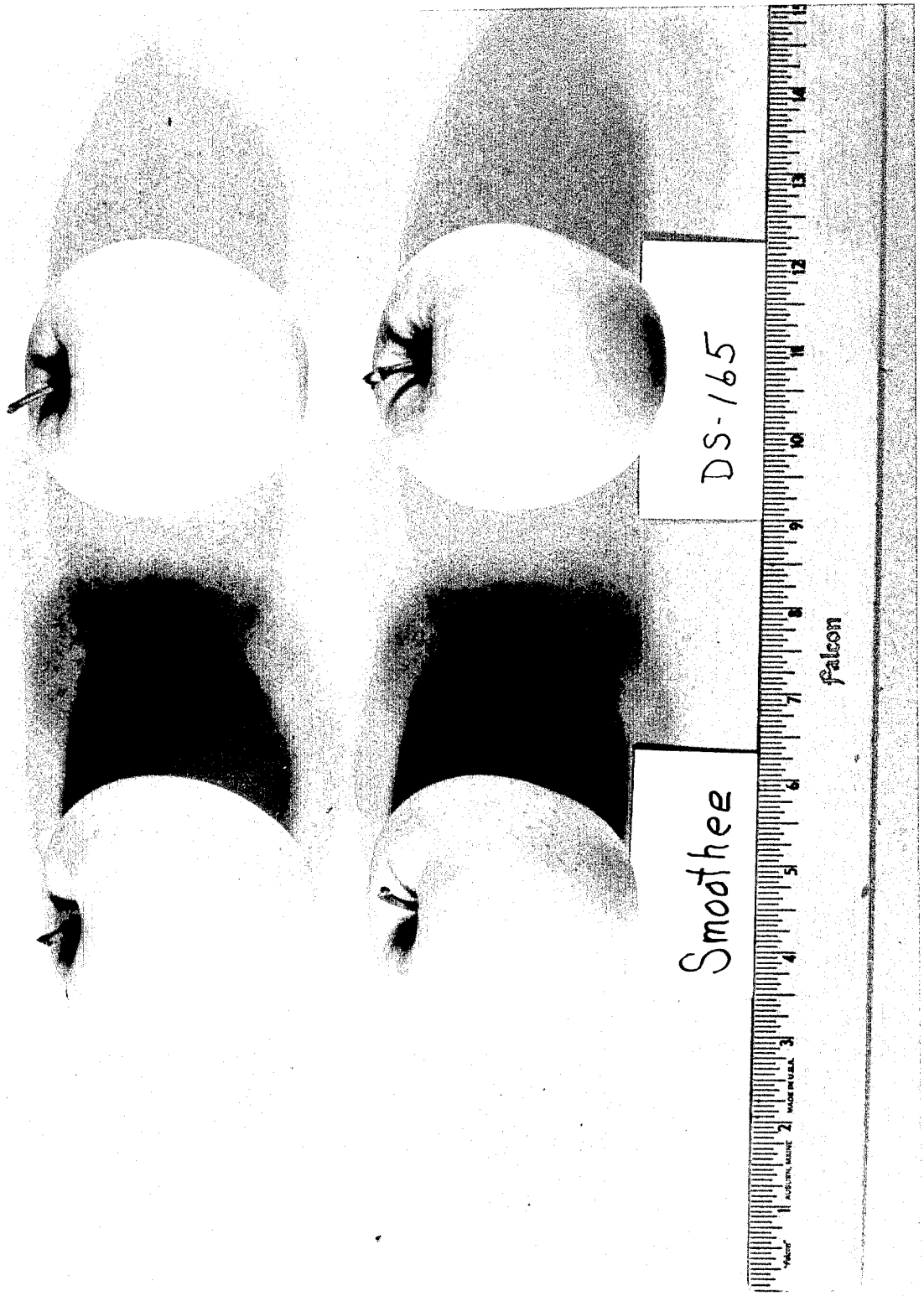
FIG. 5 shows a comparison of the fruit of 'Smoothee' with that of DS-165.
Figure 6:
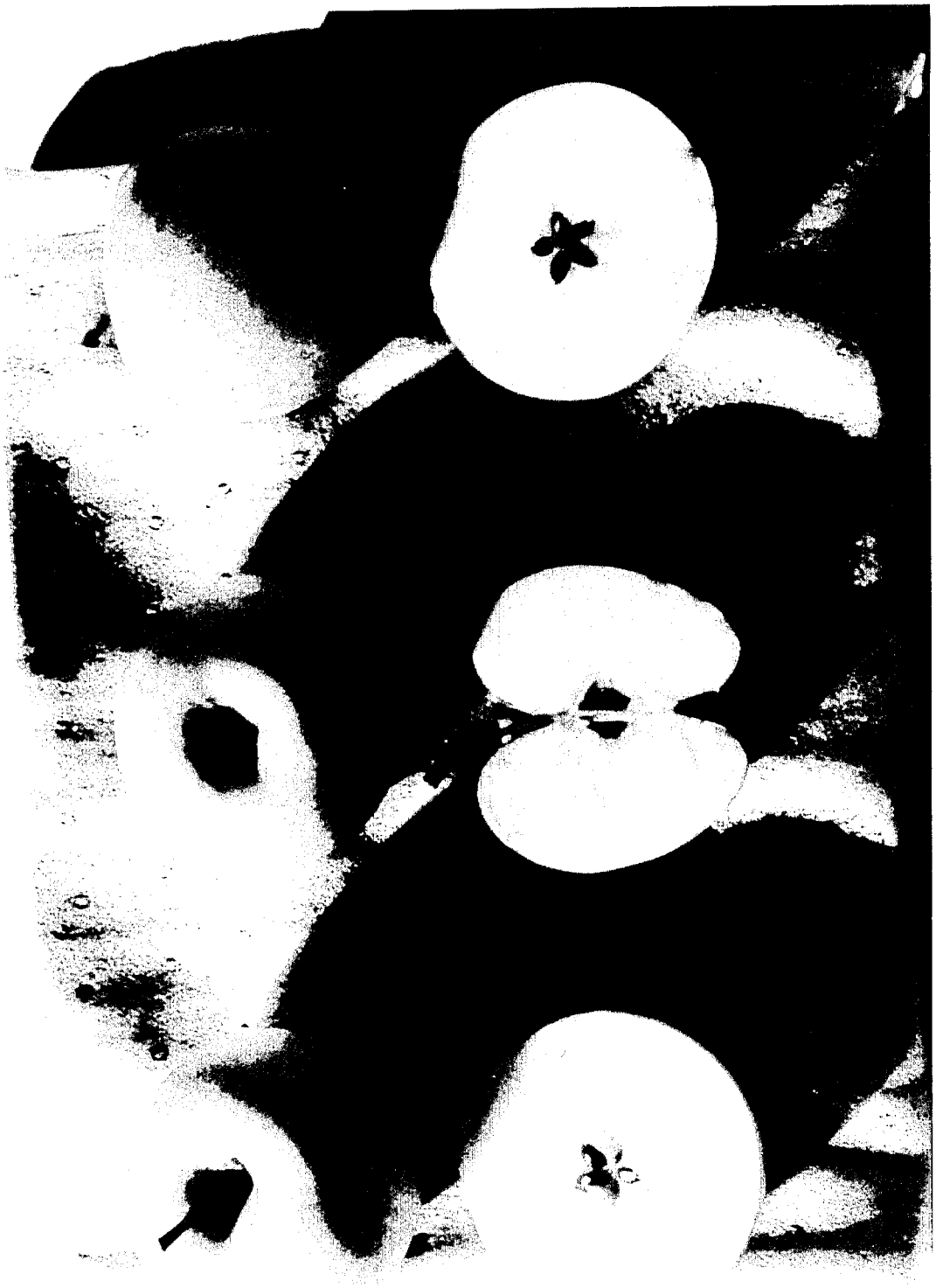
FIG. 6 illustrates the fruit of DS-165.

The following is a description of this new selection with the color designation according to the Horticultural Colour Chart issued by the British Colour Council in collaboration with The Royal Horticultural Society, except where general color terms of ordinary dictionary significance are obvious.

Flower:

*Pedicel.*—1.5 to 2.1 cm in length.
*Corolla.*—2.2 to 3.1 cm in diameter at anthesis.
*Color.*—White.
*Pollination.*—Self-pollinated.

Fruit:

*Shape.*—Ovate to slightly conic.
*Size.*—Axial diameter 6.2 to 7.0 cm. Transverse diameter 7.0 to 7.5 cm.
*Color.*—Citron Green (Pl. 763/1).
*Skin.*—Smooth, slightly waxy, with scattered, conspicuous, slightly raised, round dots.
*Stem.*—Long (1.8 to 2.0 cm) extending well beyond the shoulders, medium thickness and slightly clubbed.
*Cavity.*—Acuminate, deep, slightly russetted.

*Basin.*—Broad, medium, rounded, smooth.
*Calyx.*—Persistent, open, separated at the base; lobes slightly recurved.
*Calyx tube.*—Conical, wide.
*Stamens.*—Basal.
*Core lines.*—Meeting.
*Core.*—Closed, distant.
*Carpels.*—Elliptical, mucronate, smooth.
*Seed.*—0.7 to 0.9 cm, acuminate, smooth, dark brown.
*Flesh.*—Fine, white, crisp, juicy, very good.
*Maturity season.*—With Smoothee and Golden Delicious.
*Keeping quality.*—4–5 months in adequate storage.
*Uses.*—Excellent fresh eating, culinary, sauce, juice.
*Aroma.*—Comparable to parent variety.
*Bearing characteristics.*—Studies to date indicate DS-165 is more abundant than "Smoothee" or "Yellow Delicious" and is less likely to go biennial.
*Bruise resistance.*—Comparable to parent variety.
*Lenticels.*—Less conspicuous and less in number than "Smoothee" and "Yellow Delicious"; an average of 27 lenticels per square inch on fully-ripened fruit.

Tree:

*Growth habit.*—Vigorous, spreading, semi-spur fruiting habit and in all other characteristics similar to Golden Delicious.
*Leaves.*—Large, dark green, simple, ovate with acuminate tips, simple serrations of leaf margins, upper surface smooth and lower surface moderately pubescent, midriff red and raised, lateral veins white to light pink and slightly raised.
*Leaf size.*—Length of leaf blade — 9.0 to 10.0 cm. Width of leaf blade — 5.0 to 5.8 cm. Length-width ratio — 1.7 to 1.8.
*Petiole.*—3.0 to 3.4 cm in length, thick, reddish brown, slightly pubescent. Prominent basal bracts persist at base of petiole at abscission.
*Branches.*—30% to 50% more spurring than "Smoothee" or "Yellow Delicious"; internode distance less than "Smoothee."
*Bark.*—Comparable to parent variety.
*Winter hardiness.*—Comparable to parent variety.

*Spurs.*—Individual spurs comparable in appearance to parent variety.

*Disease and insect resistance.*—Not systematically observed, but comparable to parent variety on limited data.

*Number of spurs per linear foot of limb* (2 *year wood*).—12–13.

*Leaves per linear foot of limb* (1 *year wood*).—15–17.

In particular, this new selection is distinguished from "Smoothee" which it most closely resembles by the semi-spur type bearing habit and by the smoother, more attractive fruit finish.

What is claimed:

1. A new and distinct apple tree as shown and described, to be a true mutation of the parent cultivar "Smoothee" with a semi-spur type fruiting habit and a smoother, more attractive fruit finish.

* * * * *